United States Patent
Reed

(10) Patent No.: US 9,079,263 B2
(45) Date of Patent: Jul. 14, 2015

(54) ORTHOPEDIC FASTENER METHOD

(75) Inventor: Gary Reed, Turlock, CA (US)

(73) Assignee: RTG Scientific, Inc., Turlock, CA (US)

(*) Notice: Subject to any disclaimer, the term of this patent is extended or adjusted under 35 U.S.C. 154(b) by 215 days.

(21) Appl. No.: 13/573,137

(22) Filed: Aug. 24, 2012

(65) Prior Publication Data

US 2014/0053696 A1 Feb. 27, 2014

(51) Int. Cl.
*G05B 19/401* (2006.01)
*B23G 1/02* (2006.01)
*A61B 17/86* (2006.01)
*G05B 19/18* (2006.01)
*A61B 17/00* (2006.01)

(52) U.S. Cl.
CPC .............. *B23G 1/02* (2013.01); *A61B 17/8625* (2013.01); *A61B 17/8635* (2013.01); *A61B 2017/00526* (2013.01); *B23G 2210/08* (2013.01); *B23G 2210/48* (2013.01); *Y10T 82/10* (2015.01)

(58) Field of Classification Search
CPC .............. G05B 19/186; G05B 19/401; G05B 2219/37345; G05B 19/50296
USPC ............................................ 407/110; 82/1.11
See application file for complete search history.

(56) References Cited

U.S. PATENT DOCUMENTS

| | | | | |
|---|---|---|---|---|
| 3,561,297 | A | * | 2/1971 | Wilkins ....................... 76/101.1 |
| 4,761,891 | A | * | 8/1988 | Sugimura ....................... 33/503 |
| 4,793,220 | A | * | 12/1988 | Yamamoto et al. .......... 76/108.1 |
| 5,127,140 | A | * | 7/1992 | Oiwa et al. .................... 29/27 C |
| 6,224,299 | B1 | * | 5/2001 | Frecska et al. .................. 407/41 |
| 7,096,087 | B2 | * | 8/2006 | Sagawa et al. ................ 700/160 |
| 7,156,600 | B2 | * | 1/2007 | Panasik et al. ................ 411/411 |

* cited by examiner

*Primary Examiner* — Will Fridie, Jr.
(74) *Attorney, Agent, or Firm* — Majesty Law Group; Bernhard Kreten

(57) ABSTRACT

An orthopedic structure includes a method for making a threaded fastener with thread geometry and leading edge geometry which provides greater precision during installation. Specifically, thread pitch and tooth profiles are independently variable. A leading portion of the fastener advances bone shards forward of the forward of the fastener to reduce insertion torque and prevent the shards from residing in the upstream tooth profile for better retention.

2 Claims, 8 Drawing Sheets

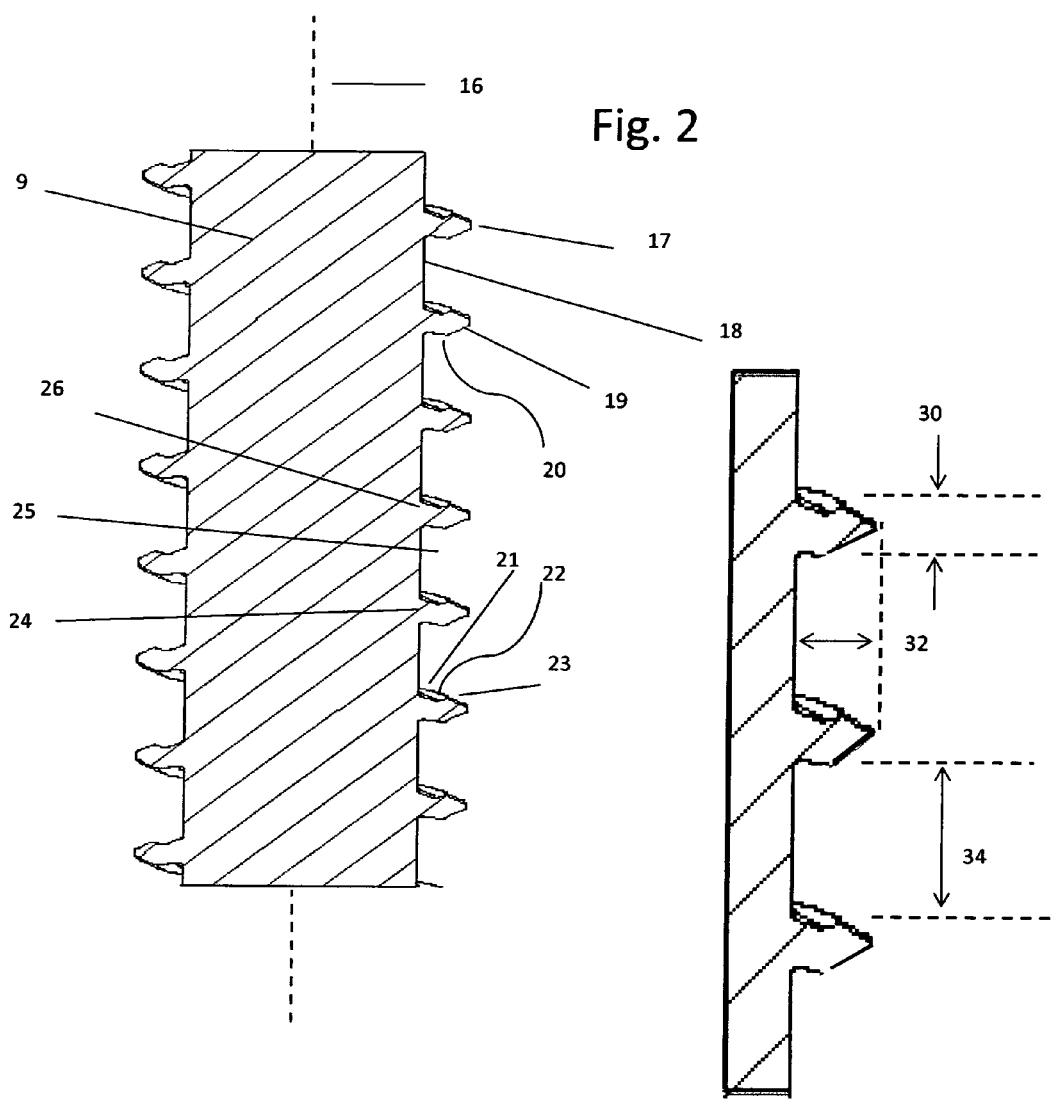

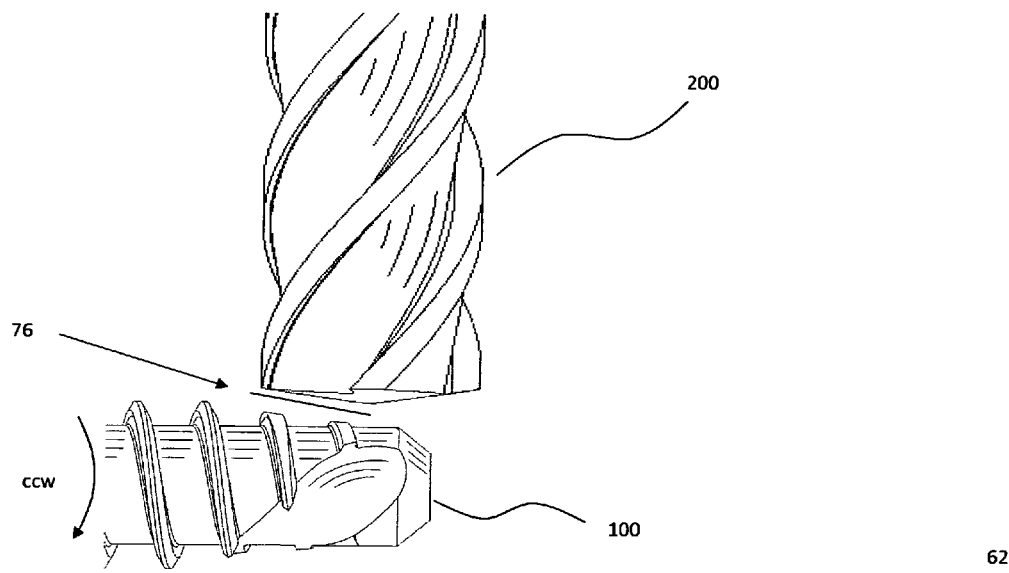
FIG. 12
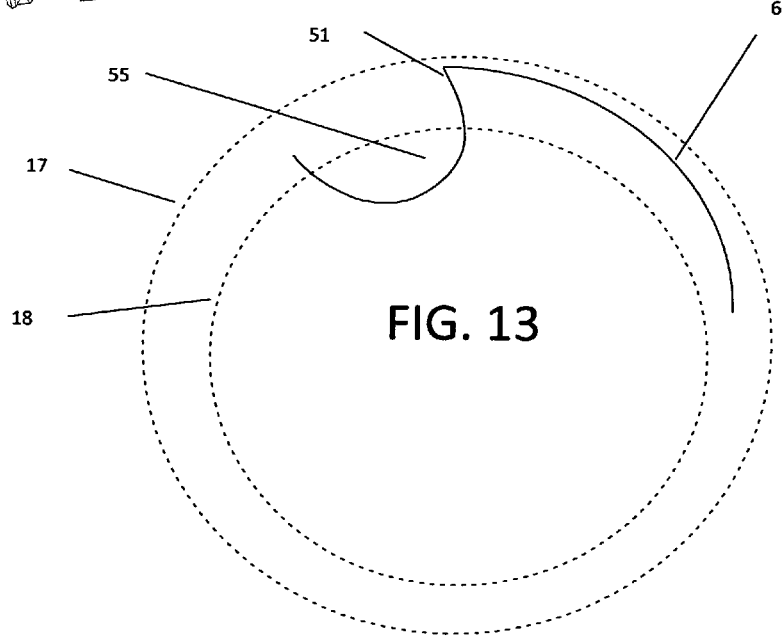
FIG. 14
FIG. 13

ORTHOPEDIC FASTENER METHOD

FIELD OF THE INVENTION

The instant invention is directed generally to devices used by surgeons primarily to embed in bone and to repair fractures. More specifically, the instant invention includes a fastener capable of rotation about an axis that is fashioned to, inter alia, resist working loose and reduce insertion torque, thereby providing both tactile feedback to the surgeon and minimize trauma at the fastening site by controlling heat buildup due to friction. The fastener reduces insertion (cutting) pressure and increases fastener tracking, thereby minimizing problems associated with misalignment.

BACKGROUND OF THE INVENTION

Surgical procedures involving fasteners on skeletal structure presently suffer from several common frailties. One is the inability to accurately orient the fastener during insertion to keep the fastener from wandering. Bone interiors have a sponge like (cancellous) texture. Even with a predrilled pilot hole, fasteners still frequently skew off the axis of the pilot hole, making it difficult to register the fastener at its distal end with another instrumentality.

Another frailty is the failure to provide a reliable thread portion that engages the bone of the patient in a manner which retards its working loose. Bone is a remarkable structure which varies both in hardness and elasticity as a function of both age and location. Loads on the fastener must accommodate not only these constraints but also the dynamics of forces generated by the patient in daily activities.

The buttress thread is presently the industry standard. Unfortunately, buttress threads are suitable for use only where load forces on the fastener are applied in one direction. (Bhandari, Design of Machine Elements (2007), page 204). Where the load forces are multidirectional or not unidirectional and axial, failure can occur. One manifestation of buttress thread failure is "toggling" where the fastener works on the bone and enlarges the hole within which the fastener resides.

Yet another frailty related to high insert torque makes it impossible to insert the screw through bone fragments without it grabbing the fragment and causing it to rotate with the screw causing significant trauma to soft tissues and a failed fixation of the fragment.

In an attempt to offset the multiple problems of buttress threads, it is common practice to design the buttress thread profile to increase retention by increasing friction. Increased friction leads to elevated temperatures during insertion, potentially damaging bone tissue. A temperature excursion greater than 116 degrees Fahrenheit (47 degrees Celsius) at the insertion site causes osteonecrosis which cannot be repaired and which the body cannot heal. And, even worse, excess heat compromises the fastener's ability to remain in place since the bone has died at the screw thread interface. As a consequence, some procedures rely on liquid cooling at the site during the drilling/insertion procedure, but, even then, the process generates so much heat that the heat generating tool can be too hot to touch because the liquid cooling is merely topical.

Since the only variables (thread pitch, crest and root diameters) in the buttress thread design are interrelated, improving retention increases friction and insertion torque, resulting in heat generation and impairing the surgeon's ability to feel the insertion torque of the fastener in a meaningful way. This still leaves the fundamental problem of the thread's inability to withstand multidirectional forces unaddressed, while creating several new problems.

The surgeon has no tactile feedback when inserting the fastener. The buttress fastener is harder to start and is prone to stripping, especially when used in conjunction with a plate. The buttress thread induces a radial force, perpendicular to the fastener's long axis, which increases the probability the bone will split or crack, making a procedure much more difficult, if not impossible. The buttress threaded fastener can wander during insertion, making its registry with an instrumentality at the distal end of the fastener a recurring problem. Wandering away from the pilot hole often results in cutting new threads in an unintended location or stripping out the pilot hole which retards healing and actually induces trauma; and, where there is a temperature excursion above 116 degrees Fahrenheit, it can also cause osteonecrosis of the adjacent bone.

The present invention's thread geometry minimizes insertion force. This allows the surgeon tactile feedback and reduces the effort required to deploy the fastener. This, in conjunction with a forward chip feeder, a centering pilot, and improved thread cutting features keep friction low, the fastener aligned and directed from wandering away from the preferred path.

The distal end of many fasteners includes a relief area (flute) designed to help cut through bone, defining a "self-tapping" fastener. Buttress thread fastener's self-tapping features a flute that is straight or at least close to in-line with the axis of the screw. That is, as the fastener is advanced, the cutting edges send the bone chip towards the head of the fastener which is into the path of the helical threads. This bone debris accumulates along the thread teeth and increases insertion torque and friction which therefore generate additional heat. The debris also makes the fastener harder to insert and provides a poor interface with the bone and the fastener.

In the present invention, the cut chips curl away from the cutting edges and are fed forward into the predrilled pilot hole in advance of the fastener because the flute is "left handed" on a right handed threaded screw. That is, as the fastener advances, the flute forces the chips forward into the pilot hole ahead of the screw. This results in exact clearance between the fastener and the portion of the bone being formed as "bone teeth" (that portion which engages the threaded fastener). The interface between the bone and fastener is therefore substantially free of the cuttings and provides healthier bone tissue adjacent the fastener to prevent additional trauma to the bone.

Another problem associated with buttress style threads is that the area between threads of the fastener is the only site of anchoring in the bone, and because of the design constraints associated therewith, this site is difficult to optimize. Stated alternatively, the metal of the fastener is orders of magnitude stronger than the retaining bone so that when failure occurs, it always involves bone trauma.

The present invention maximizes the bone being engaged while minimizing the fastener's thread, something impossible to do with a buttress thread and other common threads and common manufacturing processes. The result is less bone trauma and less bone removed to increase bone strength to retain the fastener better.

This invention discards conventional thinking and manufacturing processes in the pursuit of new and desirable functions that can be achieved from the thread profile.

Heretofore manufacturers have adopted a simple and very fast manufacturing process that produce screws that function no better than common wood screws.

BRIEF SUMMARY OF THE INVENTION

The instant invention addresses various skeletal components with fasteners in ways heretofore unattainable with an improved thread pattern which provides greater retention of bone structure and minimal damage to bone adjacent the fastener.

This invention produces a bone screw thread design that can be modified in many independent ways to produce different capabilities and functions that can contribute to better grip, greater resistance to pull-out, lower cutting and insertion pressure which reduces site temperature and causes less damage to the bone in the process. These features provide better feel for the surgeon installing the screws to prevent stripped threads, better clamping force, better fixation, and ultimately shorter healing time.

A new manufacturing process is disclosed which utilizes single-point threading in conjunction with multiple form cutting tools with different shapes and following different paths to create thread features formed by independently programmable successive cutting moves, each distinct from the others. This means that the tooth height, thickness and spacing can now each be modified independently to produce different characteristics and capabilities to greatly improve both the procedure when the screw is installed into the bone and the performance of the screw in situ.

While the method that is being disclosed forms threads of greater complexity in the process, in a production setting it is only possible because of CNC machine tools and the ability to program sequential, independent cutting moves to create unique features unknown in the prior art.

Bone fixation is very complicated because the breaks are found in an infinite variety of shapes and locations. Fasteners embedded in bone need to minimize bone trauma and removal while maximizing retention in a dynamic environment. The benefits derived from these new thread designs and a method to produce them will be very significant to the industry and patients.

OBJECTS OF THE INVENTION

Accordingly, it is a primary object of the present invention to provide an orthopedic fastener structure and method of making the fastener.

A further object of the present invention is to provide an improved threaded portion therefore.

A further object of the present invention is to provide an improved threaded portion which minimizes bone trauma, resists failure and is easy to install.

A further object of the present invention is to provide a fastener which can accommodate a plurality of different angles of attack when addressing a skeletal structure.

Viewed from one vantage point, it is an object of the present invention to provide an orthopedic fastener formed by independently modifying tooth height, thickness and spacing, thus altering said faster's characteristics and capabilities.

Viewed from another vantage point, it is an object of the present invention to provide an orthopedic fastener formed by: independently modifying tooth height, thickness and spacing, thus altering said fastener's characteristics and capabilities, whereby pitch and major and minor tooth thread diameters are independently variable to facilitate matching fastener thread profiles with corresponding bone tooth profiles as a function of bone density and site of fastener deployment to improve fastener purchase and increase resistance to pull out forces.

Viewed from the previous vantage point, it is an object of the present invention to provide a fastener further including forming a chip cutting flute at a distal end thereof, said chip cutting flute having leading cutting edges defining a cutting thread pattern disposed on said distal end and spiraling helically in a direction opposite from a thread pattern disposed on a remainder of the fastener, said thread pattern disposed on said remainder of the fastener defining a substantially non cutting, interlocking thread pattern whereby said cutting flute forms the interlocking thread pattern in the bone thereby reducing friction upon fastener insertion and minimizing heat buildup while providing greater sensitivity during fastener installation, reducing installation torque and possible misalignment which otherwise causes unnecessary bone removal and thread stripping while resisting breaking loose bone fragments during installation.

Viewed from the previous vantage point, it is an object of the present invention to provide a fastener further formed by disposing the interlocking thread pattern spirally along the fastener, interrupted by a substantially cylindrical fastener shaft such that said fastener shaft defines a cylindrical wall spiraling along a length of said fastener and interrupted by said interlocking thread pattern, whereby said interlocking pattern retards toggling of the fastener and minimizes radial forces while resisting multidirectional forces and bending moments which otherwise could cause fastener upheaval Viewed from the previous vantage point, it is an object of the present invention to provide a fastener further forming an abutment surface adjacent a proximal end of said fastener, defining an impediment to further fastener advancement and means to induce clamping of said fastener in an orthopedic environment.

Viewed from a previous vantage point, it is an object of the present invention to provide a fastener further forming an interference fit adjacent a proximal end of said fastener, defining an impediment to further fastener advancement and means to induce clamping of the fastener in an orthopedic environment.

Another vantage point contemplates an orthopedic fastener, comprising, in combination: a shaft having a proximal end provided with means for advancing said fastener and means for impeding fastener advancement, said shaft having a thread pattern providing interlocking means wound about said shaft, said thread pattern interrupted by intervening walls of said shaft, a thread forming means on a distal end of said shaft, said thread forming means having a thread pattern opposite from said thread pattern having said interlocking means, and a pilot at said distal end of said shaft adjacent said thread forming means, said thread forming means including means to advance bone fragments away from said fastener.

Another vantage point contemplates a process for forming an orthopedic fastener, the steps including: forming an interlocking thread on a substantially cylindrical stock of orthopedic grade substrate, forming first and second facets of said interlocking thread on said substrate with a first cutting tool while inducing relative rotation between the substrate and the first cutting tool, forming a third facet on said substrate with a second cutting tool while still inducing rotation, and forming fourth and fifth facets on said substrate with a third cutting tool while inducing counter rotation.

BRIEF DESCRIPTION OF THE DRAWINGS

These and other objects will be made manifest when considering the following detailed specification when taken in conjunction with the appended drawing figures.

FIG. 2 is a sectional view of a portion of the fastener.

FIG. 3 is a further sectional view of the fastener geometry, detailing relationships of the thread.

FIG. 12 shows a portion of a cutting tool which forms one aspect of the cutting threads at the flute.

FIG. 13 shows an end view of the cutter and its talon shaped leading edge formed by the FIG. 12 tool.

FIG. 14 is a side view of the cutter formed by the FIG. 12 tool.

DESCRIPTION OF PREFERRED EMBODIMENTS

Figure 1:
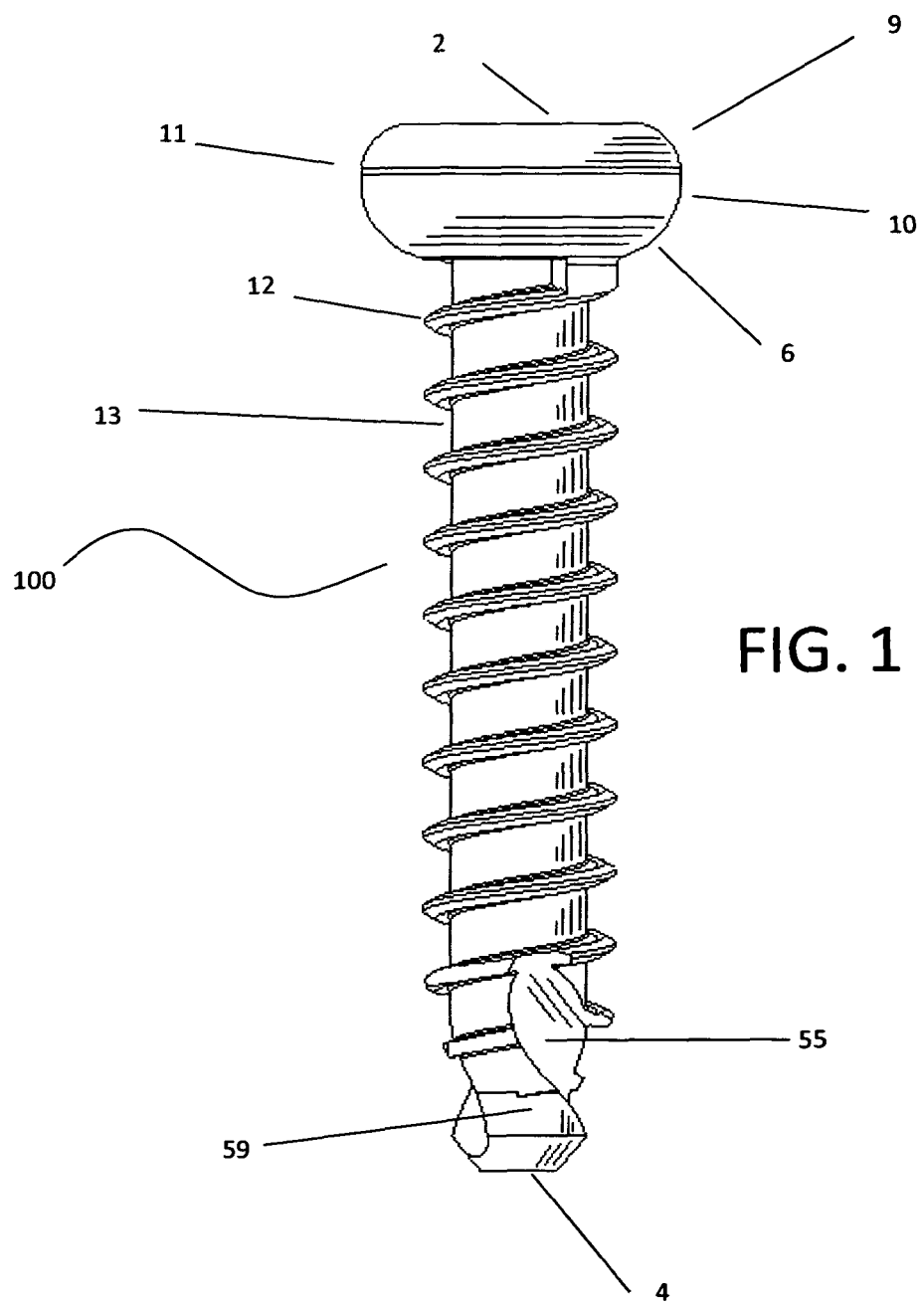
FIG. 1 is a side view of the fastener.

Considering the drawings, wherein like reference numerals denote like parts throughout the various drawing figures, reference numeral 100 is directed to the orthopedic stabilization fastener according to the present invention.

The features of the screw threads in FIG. 1 include: the head 2 (defining a proximal end) of the screw is comprised of radii 9 and 10 converging at apex 11 to form the outside diameter of the head 2. The head 2 may include a lower wall 6 which defines an abutment surface so that, when the fastener 100 is fully installed, the abutment surface 6 bears against a supporting surface (e.g. patient's body or plate) and induces the compressive load 5 shown in FIG. 11. As load 5 in induced, centering points 36 FIG. 11 of screw teeth 24 are loaded against the bottom centering points 37 of bone teeth 25 which prevents radial inward or outward forces 3 from axis 16 of the screw. Likewise, load vector 1 FIG. 11 induces screw centering point 38 against bone centering point 39. If the fastener is to be countersunk, the apex diameter 11 of the fastener 100 approximates the major thread (crest) diameter 17 and the compressive load 5 is then caused by interference fit relying on a thread portion immediately adjacent the head 2.

More specifically, the last turn of the thread 12 (nearest head 2) either has both a different pitch and/or tooth thickness which provides resistive clamping. Up until this abutment, the fastener is substantially free turning due to low friction geometry. This provides tactile feedback to the surgeon. Right hand threads 12 are helically wound along shaft 13 to produce the thread pitch. The distal end 4 of the screw features a pilot 59 incorporating chip dispersing flutes 55 having a left-handed spiral orientation.

Figure 4:
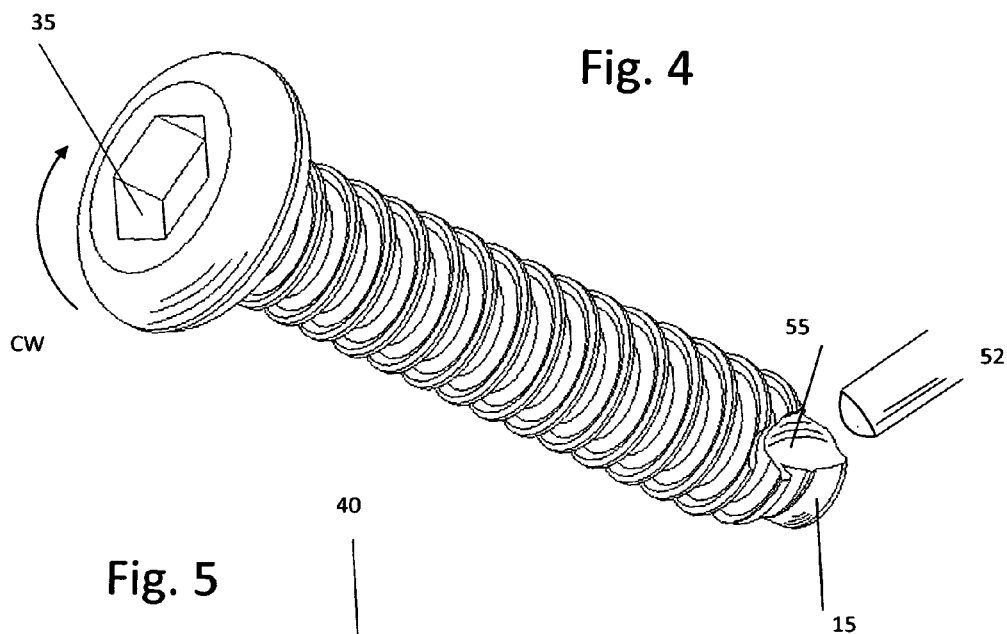
FIG. 4 shows the fastener in perspective.

FIG. 4 shows the internal Hex drive socket 35 at the proximal end of the screw. FIG. 2 depicts a cross section 9 of the threaded portion of the screw shaft with an axis 16 passing through core of the shaft.

Thread 24 extends away from thread root 18 (shaft exterior 13) defining the major thread diameter 17. Bone tooth 25 is formed by the boundaries of thread root 18, screw thread tooth 24 and screw thread 26. The thread root 18 (shaft exterior 13) defines a substantially continuous cylindrical wall, helically spiraling between the shaft threads and interrupted only by the helically wound threads 12.

The outward protrusion of the screw threads 32 (FIG. 3) and the thickness of the screw threads 30 coupled with the improved cutting edges of the screw teeth 51 (FIGS. 8, and 10) created by the left hand concave spiral chip dispersing flute 55 (FIGS. 1, 4, 8, and 10) determine the cutting and insertion torque of the screw. This is an important and significant improvement as it provides the surgeon with a desired tactile interpretation of the interface with the bone. This also helps the surgeon determine how tight the screw is and how much load is actually being applied for compression. Current technologies require so much torque to install a fastener that the surgeon can barely tell what is really happening. This often results in stripped threads or loose screws.

Another key feature of this new thread profile in FIG. 3 is the manufacturing method with the options to easily change the outward protrusion 32 of the screw thread teeth, the spacing 34 between adjacent teeth which determines the dimension ("volume") of the bone tooth 25, and the thickness 30 of the screw thread teeth.

The dimension (volume) of the bone tooth 25 is a very important issue because the metal screw thread is significantly stronger than the bone. By having the ability to create a more equal strength balance between the two, it is now possible to provide a screw to bone interface that can accomplish a much better and more stable grip in the bone.

By increasing the screw thread protrusion 32 it is possible to produce a screw thread that can have increased purchase in less dense bone. By reducing the bone tooth width 34 of the bone tooth 25, it is possible to create a smaller pitch for better purchase in bone with a very thin cortical wall, yet at the same time maximize cancellous bone tooth dimensions that require wider bone teeth 25 and greater outward protrusion of screw teeth 32. In all prior threads wherein common tooth profiles have been created by a single point cutting or rolling tool it was not possible to have these options.

Figure 5:
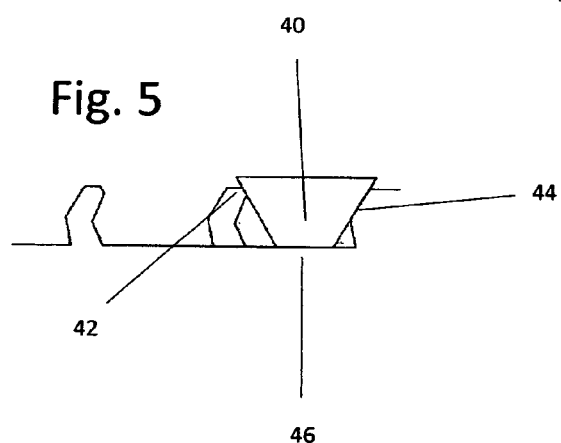
FIG. 5 is a view of a first step in the thread formation.

The step shown in FIG. 5, for this new manufacturing method of multiple cutting tools for material removal teaches that a special form cutting tool 40 creates screw thread facets 42, 44, and root 46.

Figure 6:
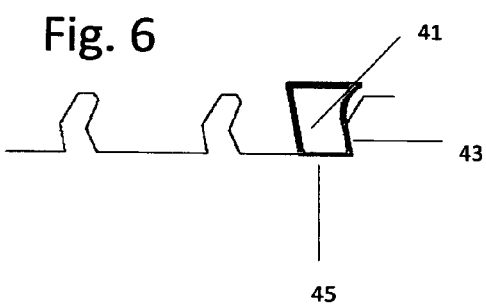
FIG. 6 is a view of a second step in thread formation.

The step shown in FIG. 6, for this new manufacturing method of multiple cutting tools for material removal teaches that a special form cutting tool 41 creates screw thread facets 43, and additional root 45.

Figure 7:
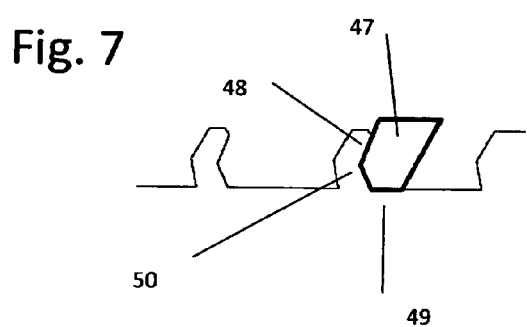
FIG. 7 is a view of a third step in thread formation.

The step shown in FIG. 7, for this new manufacturing method of multiple cutting tools for material removal teaches that a special form cutting tool 47 creates screw thread facets 48, and additional root 49. The FIGS. 5 and 6 steps occur with relative rotation in one direction; FIG. 7 step is counter rotated.

The significance of roots 45, 46 and 49 is that these surfaces define a substantially wide cylindrical wall which helically spirals along the fastener, interrupted only by the interlocking teeth, so that, bending forces experienced by the fastener are distributed along these roots and therefore also along the bone teeth in tangential registry therewith to prevent any motion because of the increased surface area which is devoid of any sharp surfaces which would otherwise define pressure points—as in the prior art.

Figure 9:
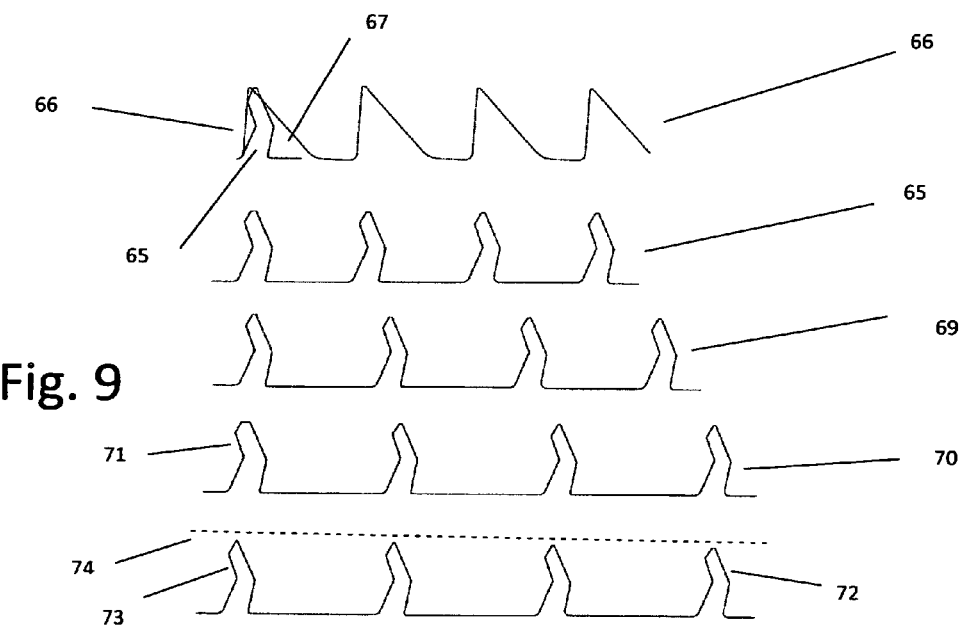
FIG. 9 illustrates the amount of bone tissue that is lost with a conventional buttress thread as compared with the present invention, setting aside the fact that the present invention does not require uniform spacing of adjacent threads (pitch), as in the buttress thread. Also shown are examples of increasing thread pitch while maintaining the same thread height.

FIG. 9 illustrates the benefits of this three step cutting process when compared with a buttress thread. As shown, two thread profiles are shown with their pitches in registry. One buttress thread is superposed over one thread of the present invention. As shown, the buttress thread removes at least one third more bone in this depiction, but it should be pointed out that the thickness 30 (FIG. 3) of the present invention's thread could be reduced to the thickness of a thin blade when the appropriate material has been chosen for the fastener. When the thickness 30 has been optimized (minimized), a maximum volume of bone tooth is available for maximum grip and minimum trauma while reducing friction and insertion force.

Figure 11:
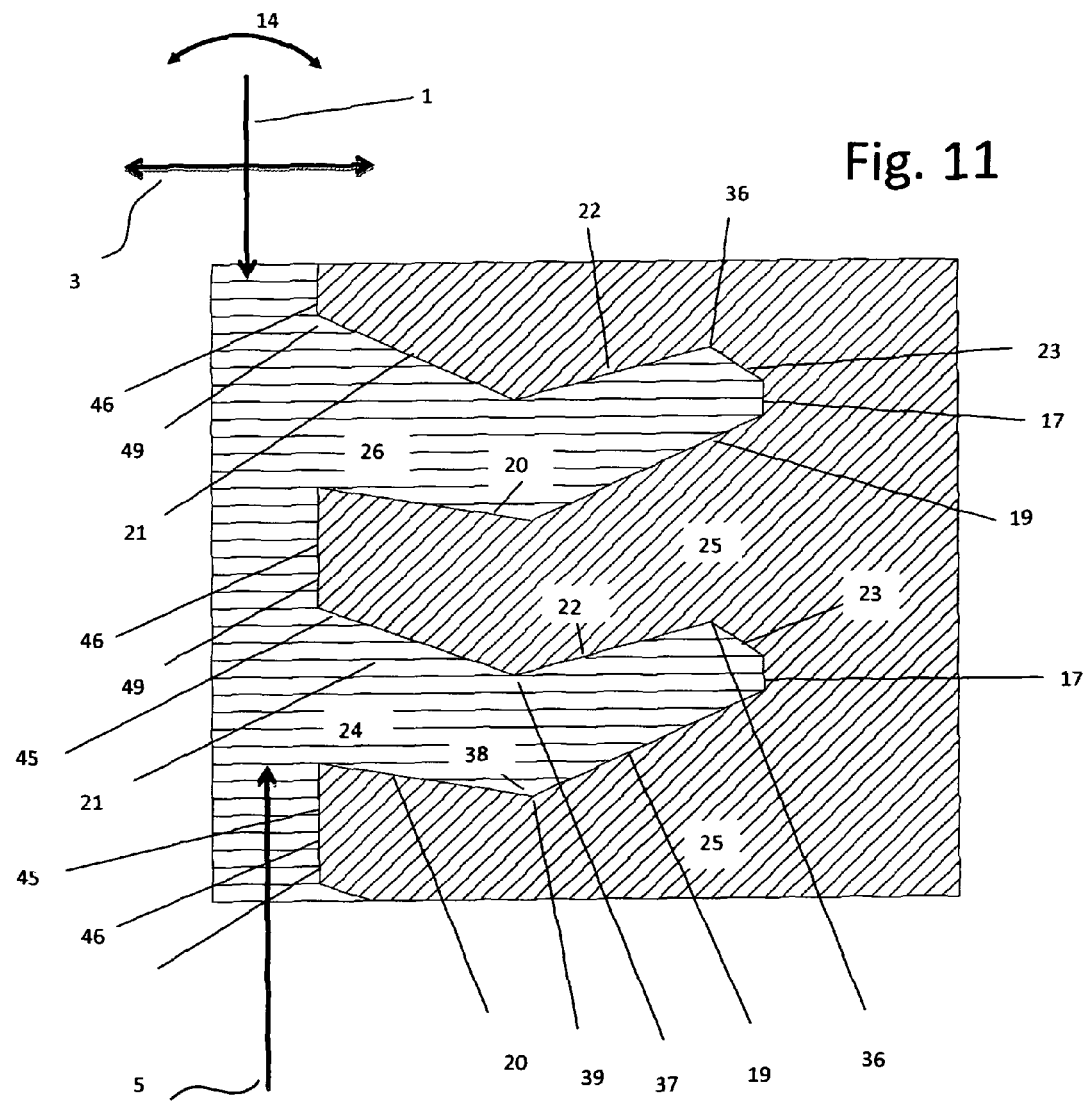
FIG. 11 illustrates force vectors one of which is a reaction forces when the fastener has reached the moment of compressive tightening.

Yet another significant feature of this invention is the mechanical interlocking capability of this thread profile. In essence the bone thread tooth 25 is interlocked between screw threads 24 and 26. This is illustrated in FIGS. 2 and 11. Reaction forces, responding to the load 5 induced upon tightening, are distributed along the various facets/flanks of the fastener. As shown, forces are centered, screw flanks are interlocked with bone teeth 25 surfaces and centering points 36, 37, 38, 39 at the juncture of flanks cooperate to prevent strain and resist spreading in either axial load or torsional load. Specifically, flanks 19 and 20, 21 and 22, 22 and 23 operate in pairs such that the intersection of the pairs define centering points for load distribution and force equalization.

Note the screw tooth facet 20 is at a lesser angle from axis 16 than screw thread facet 21, This means that bone screw tooth 25 becomes trapped "inboard" (between the apex 36 (FIG. 11) formed at the juncture of facet 22 and 23 on one side, and thread root 18 and screw thread facets 20 on the other side). This produces an instant mechanical interlock between the fastener screw threads 24, and 26 along thread 12, and the bone thread tooth 25. The significance of this feature has far reaching value. In bone it is best to produce an interface that is neither radial spreading nor radial drawing when the screw is tightened to reduce trauma to the bone.

Current bone screw threads create harmful compressive loads that can crack the bone or at least compress the living bone excessively adding to the trauma. In the present invention, these problems are resolved. Here, the relationship of the teeth facets (flanks) 19 and 20 can be "adjusted" (dimensionally changed) relative to facets (flanks) 21, 22 and 23 to alter fastener tooth thickness 30 and separation between adjacent teeth via modifying the bone tooth gap 34, for example, to provide maximum bone engagement and optimize compression pressure for the entrained bone located between fastener teeth.

This invention with its improved cutting edges, chip removal, reduced tooth width and less bone removed produces new interface characteristics with the bone while providing the surgeon with the best possible feel during the initial threading and torquing sequence.

Figure 8:
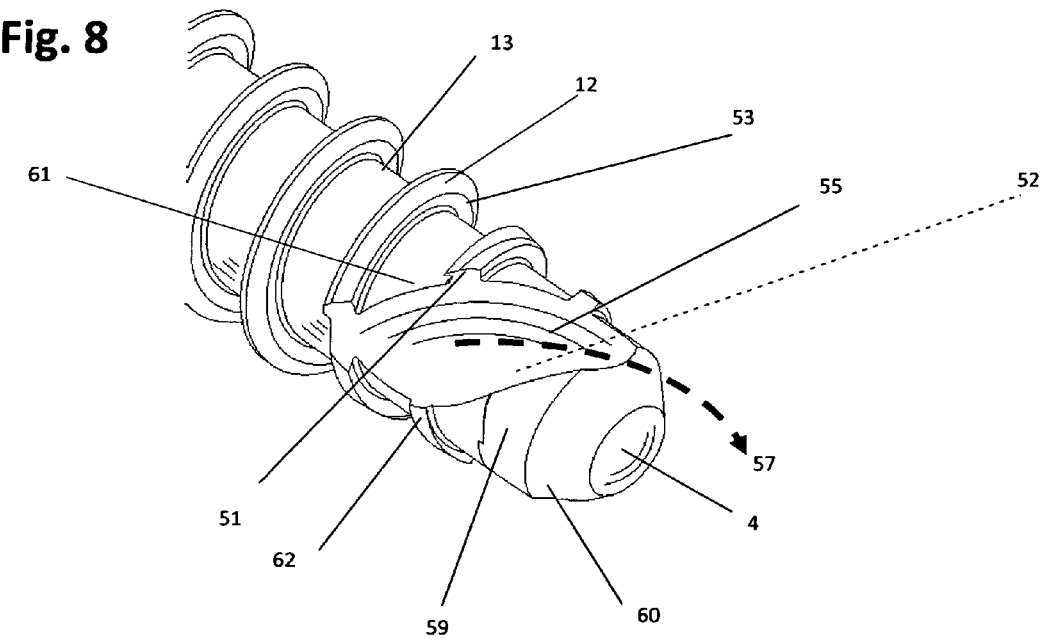
FIG. 8 details the leading end of the fastener which initiates insertion.
Figure 10:
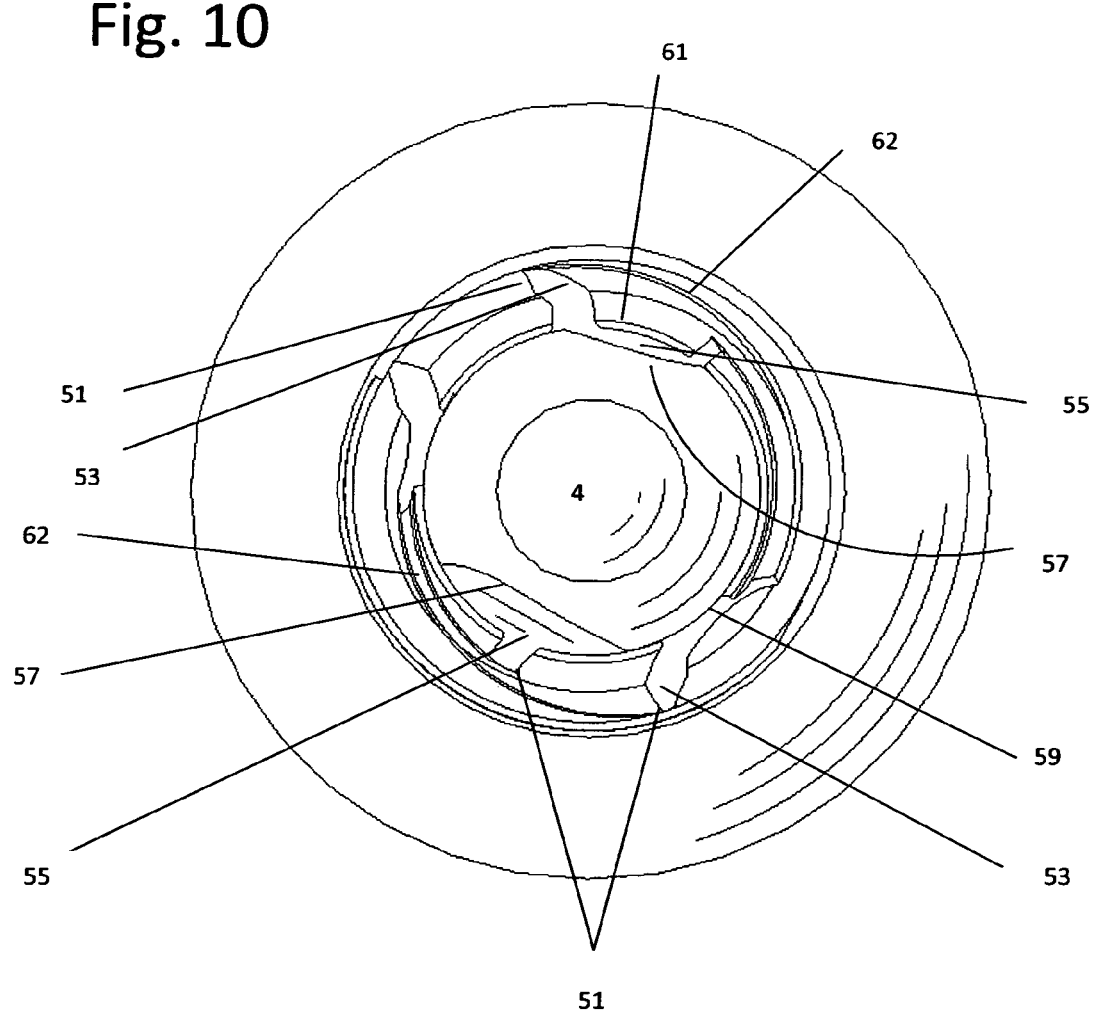
FIG. 10 is a view of the distal end of the fastener, showing details of the pilot and left handed chip dispersal flute and improved self-tapping features along with an eccentric relief starting at the leading cutting edge of each thread formed by a first left handed flute.

FIGS. 8 and 10 show pilot 59 with the concave spiral chip dispersing flute 55 that angles from the axis of screw 100 at an approximately 45°, (reference numeral 52). Chip dispersing flute has a portion which opens through the outside diameter of pilot 59 and extends in a left handed helical transition a short distance (1 or more threads) towards the proximal end of the screw. The chip dispersing flute gently transitions into shaft 13 and threads 12. The actual cutting of chips are caused by sharp leading cutting edges 51 formed by the left handed helical chip dispensing flute 55 and having slightly blunted trailing cutting edges 53. The concave radius of flute 55 thus produces a sharp leading cutting edge 51 at the intersection of threads 12 and flute 55 at the major diameter of threads 12. Eccentric radial relief edges 62 combine with sharp edges 51 to approximate a talon-like contour wherein the major diameter decreases in diameter as it trails away from edges 51 to provide leading edges that can easily cut the bone producing chips that curl from the cutting edges and transition out of the concave chip dispersing flute. Said eccentric relief gradually reduces the height of threads 12 until interrupted by a next left hand flute where upon the eccentric relief starts again at the major diameter of the next helical thread 12 as it continues on the opposite side of the second left hand flute and concludes at a decreased height as it ends back at the left hand side of the next flute.

FIG. 12 reveals how eccentric radial relief 62 is formed by a special cutter 200 turning in a clockwise direction as the screw is rotated in a counter clockwise direction as it slowly moves downward 77 to form eccentric reliefs 62. The cutting end of the cutter is shaped at an angle 76 to cut a slight taper on the outside diameter of threads 12 extending from the distal end of the threads upwards towards the proximal end to coincide with the length of the chip dispersal flute 55.

This is illustrated in FIG. 13 as a cross section of the "talon" shaped thread cutting profile produced by the combination of flute 55 creating the sharp cutting tip 51 and eccentric relief 62 by rotating cutter 200 while it moves in a downward direction 77 until it reaches the back edge of the next flute 55. At this point the cutter 200 moves upward to start the same process again at the beginning edges of the next side of flute 55 and continuing this process until the cutter has completed a 360° rotation and all distal threads have been treated by cutter 200 with eccentric radial reliefs 62.

These features combine to cut clean threads and move the chips along chip path 57 pushing them forward through the drilled pilot hole ahead of the advancing screw as it is helically turned into the bone. The leading edge 61 of the transition of flute 55 and root 13 produces a precision fit within the inside diameter of the drilled pilot hole to provide a positive chip removal scraping action as screw 100 turns inside the drilled pilot hole. This scraping action forces the chips down and out of the precision fit of the pilot inside the drilled hole. The benefit here is that the leading edges 51 cause the chips to curl forward and follow the contour of the flute 55 forward, and out the end of chip path 57 away from the path of the advancing threads.

Figure 16:
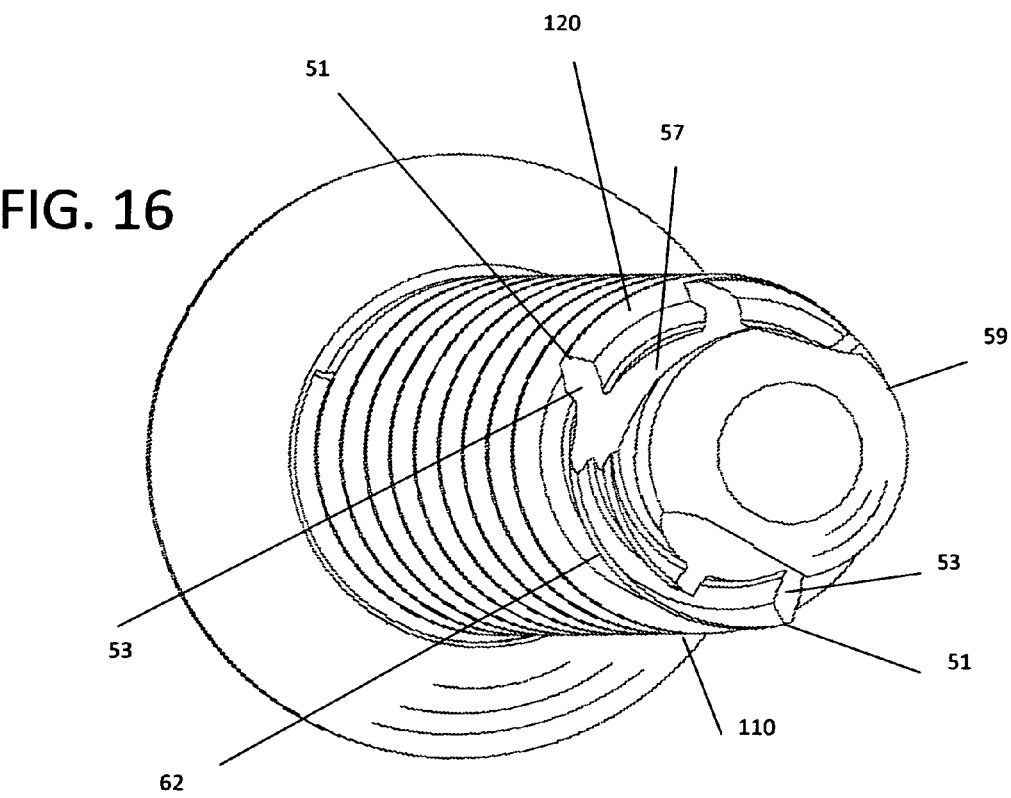
FIG. 16 is an end view of the double-start thread cutting edges defined by the flutes.

Stated alternatively, as the fastener is inserted clockwise CW (FIGS. 4, 8 and 10), the leading cutting edges 51 progressively shave thin ribbons of bone, advancing them forward and pushed by the leading edge 61 in the direction 57. This creates a true self tapping screw and also prevents the chips from being drawn into the advancing screw threads and the bone. This results in much lower cutting pressure, cleaner threads and less damage to the bone. (If the chips can't get out of the way they get drawn into the path of the threads and get crushed into the surrounding bone. If this happens, the trapped chips can kick off an inflammation process resulting in the immune system attacking the chips as foreign bodies with eventual absorption, causing voids next to the threads eventually resulting in loosening of the screw threads 12.) FIG. 16 shows a cutter and pilot for a dual start, dual thread fastener.

The pilot 59 has a substantially circular, planar, distal end 4 interrupted by portions of the chip dispensing flutes 55 shown in the drawings. More or fewer chip dispensing flutes 55 can be provided so long as they are symmetrically oriented along the periphery. A marginal periphery 60 provides a radiused transition between the planar distal end 4 and the cylindrical shaft 13. This radiused transition forces the fastener 100 to remain in the predrilled pilot hole, thereby assuring registry of the fastener 100 with another surgical instrumentality (such as a plate) on the distal end of the fastener.

In use, preferably a pilot hole is predrilled and the fastener 100 is oriented there over. The radius 60 of the pilot 59 nests within the predrilled pilot hole. Advancement of the fastener by clockwise rotation (CW) causes the chip dispensing flutes 55 and their leading (left handed) cutting edges 51 to incrementally shave bone shards away from the fastener, with leading edge 61 pushing the shards forward into the concavity and forward into the predrilled hole along path 57, after having been chipped off by the trailing cutting edges 53. Bone is thus threaded in conformance with the fastener's tooth profile. As the fastener 100 advances into the bone, the bone teeth 25 provide positive engagement with the fastener 100 without perceptible friction (deleterious heat buildup) or unwanted radial forces experienced by the surgeon who—unlike the prior art—can advance the fastener with very little effort.

This gives the surgeon precise information on the progress of the procedure. The radiused wall 60 on the pilot tracks the predrilled hole precisely without deleterious wandering and trauma to the adjacent bone. The fastener's threads are concomitantly self-interlocking with the bone teeth up until the fastener is nearing complete embedment. Then, the abutment surface 6 in the bottom of the fastener head contacts cortical bone on the outer periphery of the predrilled hole causing vector 5, FIG. 11.

This contact induces a change in force which is perceptible to the surgeon unlike the prior art. The surgeon thus has better "feel" to sense and adjust the compression/torque most beneficial to the procedure. As mentioned above, the same improved tactile feedback exists where the fastener does not have a head, but instead is to be countersunk. Further, an interference thread 71 adjacent the proximal end 6 provides additional feedback and retention. This is accomplished by increasing the width 30 of one or more thread teeth near proximal end 6 that creates a clamping load on the bone tooth 25 (by decreasing dimension 34) against bone teeth 25 that were formed by thread cutting features at the distal end of the screw.

An alternative (or supplement to this interference thread) would be to change (increase) the thread major diameter near the proximal end 73 while maintaining the original height 32 at the distal end 72, which provides an interference fit in a different way. This (taper) is recognized by reference line 74 and provides increasing drag along the major diameter of the threads as the screw is advanced into the bone. Further, the fastener with a head can benefit from either or both types of interference fit if desired.

Additionally, in the event of side loading (toggling") force vectors 3 FIG. 11 are constrained by the interlocking capability of the screw threads 24 and 26 that are instantly and mechanically interlocked with bone teeth 25. Unlike prior art, loading screw 100 from one side or the other does not create a gap between the screw and bone on the opposite side. This is commonly referred to as "toggling" and often results in failure of the screw to bone interface.

A somewhat similar issue occurs when a bending moment 14 is applied to the screw 100 wherein the resulting force causes a similar screw produced with buttress or V style threads to yield to the force at the root diameter (groove) between two threads. When yielding occurs, the thread root acts as a radial groove around the circumference of the screw and the full load will focus on the weakest spot (a single thread groove) near the apex of the bending moment resulting in failure of the core of the screw. Unlike this frailty found in all other thread forms, this instant invention has thread roots that are cylindrical in form and lack thread grooves thereby spreading the load of a bending moment uniformly along the shaft of the screw. This provides a more durable and reliable screw resistant to bending.

Figure 15:
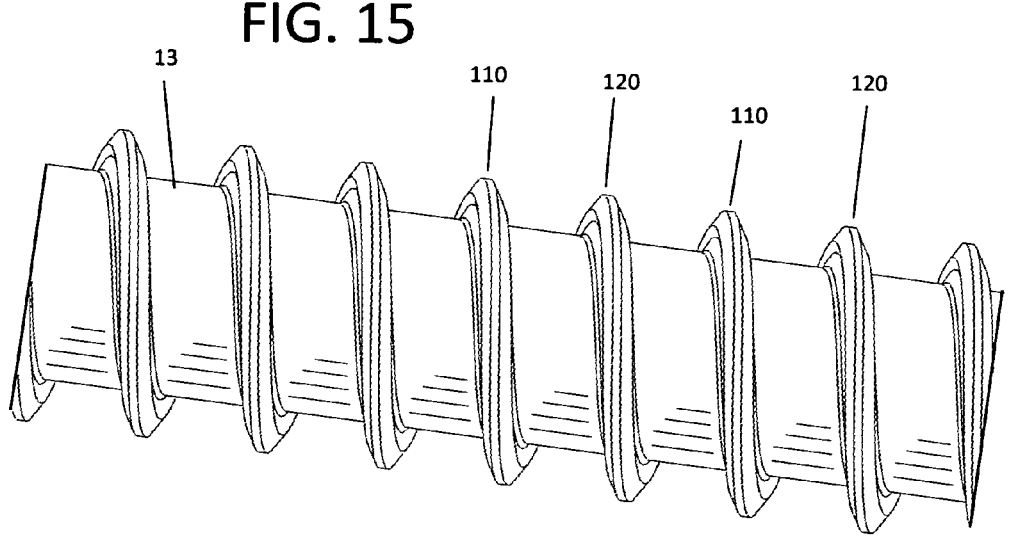
FIG. 15 is an end perspective of a double-start thread fastener.

FIGS. 15 and 16 teach the use of a dual thread pattern. A first interlocking thread 110 spirals along cylindrical shaft as before, but a second interlocking thread 120 also spirals along shaft 13. Note the cutter edges 51 and other details of FIGS. 8 and 10 appear here as well as the pilot 59. Thus adjacent threads of first interlocking thread 110 have a second thread 120 interposed there between. This means the pitch of this fastener is twice that of the previously described fastener, which results in faster insertion (axial advancement) of the dual thread design. Where time is of the essence, this is an important feature, and operations such as this are best concluded expeditiously for many reasons, such as asepsis, greater productivity and minimal time of patient anesthesia.

Moreover, having thus described the invention, it should be apparent that numerous structural modifications and adaptations may be resorted to without departing from the scope and fair meaning of the instant invention as set forth hereinabove and as described hereinbelow in the claims.

I claim:

1. A process for forming an orthopedic fastener wherein the orthopedic fastener is adapted to be inserted into a skeletal structure, the steps including:
    forming an interlocking thread on a substantially cylindrical stock of orthopedic grade substrate,
    forming first (19) and second facets (23) of said interlocking thread on said substrate with a first cutting tool while inducing relative rotation between the substrate and the first cutting tool and providing clearance for a second cutting tool,
    forming a third facet (20) on said substrate with a second cutting tool while still inducing rotation, and providing clearance for a third cutting tool,
    forming fourth (21) and fifth facets (22) on said substrate with a third cutting tool while inducing counter rotation whereby counter rotation improves thread profile.

2. The process of claim 1, further including counter rotating said substrate and forming a self-tapping cutting means on a distal end of said substrate thereby forming a fastener which advances bone fragments forward away from said interlocking threads.

* * * * *